US010710890B2

United States Patent
Burton et al.

(10) Patent No.: US 10,710,890 B2
(45) Date of Patent: Jul. 14, 2020

(54) EMM-37 MATERIALS AND PROCESSES AND USES THEREOF

(71) Applicant: ExxonMobil Research and Engineering Company, Annandale, NJ (US)

(72) Inventors: Allen W. Burton, Stewartsville, NJ (US); Hilda B. Vroman, Piscataway, NJ (US); Eugene Terefenko, Center Valley, PA (US)

(73) Assignee: ExxonMobil Research & Engineering Company, Annandale, NJ (US)

( * ) Notice: Subject to any disclaimer, the term of this patent is extended or adjusted under 35 U.S.C. 154(b) by 0 days.

(21) Appl. No.: 16/254,794

(22) Filed: Jan. 23, 2019

(65) Prior Publication Data

US 2019/0256365 A1    Aug. 22, 2019

Related U.S. Application Data

(60) Provisional application No. 62/632,681, filed on Feb. 20, 2018.

(51) Int. Cl.
| | | |
|---|---|---|
| *C01B 39/48* | (2006.01) | |
| *B01J 29/70* | (2006.01) | |
| *B01J 20/18* | (2006.01) | |
| *B01J 20/28* | (2006.01) | |
| *B01J 20/30* | (2006.01) | |
| *B01J 35/10* | (2006.01) | |
| *B01J 37/00* | (2006.01) | |
| *B01J 37/04* | (2006.01) | |
| *C07D 207/06* | (2006.01) | |
| *C10G 11/05* | (2006.01) | |
| *C10G 45/64* | (2006.01) | |
| *C10G 47/16* | (2006.01) | |

(Continued)

(52) U.S. Cl.
CPC ............... *C01B 39/48* (2013.01); *B01J 20/18* (2013.01); *B01J 20/183* (2013.01); *B01J 20/28071* (2013.01); *B01J 20/3064* (2013.01); *B01J 20/3078* (2013.01); *B01J 29/70* (2013.01); *B01J 35/1038* (2013.01); *B01J 37/0018* (2013.01); *B01J 37/04* (2013.01); *C07D 207/04* (2013.01); *C07D 207/06* (2013.01); *C10G 11/05* (2013.01); *C10G 45/64* (2013.01); *C10G 47/16* (2013.01); *C10G 50/00* (2013.01); *C01P 2002/72* (2013.01); *C01P 2002/77* (2013.01); *C01P 2006/14* (2013.01)

(58) Field of Classification Search
CPC . C01B 39/48; B01J 20/18; B01J 29/70; C01P 2002/72; C01P 2002/77; C01P 2006/14
See application file for complete search history.

(56) References Cited

PUBLICATIONS

Jo et al, "A Zeolite Family Nonjointly Built from the 1,3-Stellated Cubic Building Unit", Angew. Chem. Ind. Ed. (2018) pp. 2199-2203, (Year: 2018).*

(Continued)

*Primary Examiner* — David M Brunsman
(74) *Attorney, Agent, or Firm* — Priya G. Prasad (57) ABSTRACT

The disclosure is related to EMM-37 materials, processes of making, and uses of the same as well as structure directing agents useful for the preparation of the EMM-37 materials, processes and intermediates for making such structure directing agents.

14 Claims, 2 Drawing Sheets

(51) Int. Cl.
*C10G 50/00* (2006.01)
*C07D 207/04* (2006.01)

(56) References Cited

PUBLICATIONS

Kapaca et al, "Small Pore Aluminosilicate EMM-37: Synthesis and Structure Determination Using Continuous Rotation Electron Diffraction", Inorg. Chem. (2019) 58, 12854-12858 (Year: 2019).*

Broach et al, "Structure of the K+ and NH4+ forms of Linde J", Microporous and Mesoporous Materials, 143 (2011) 398-400 (Mar. 2011) (Year: 2011).*

* cited by examiner

EMM-37 MATERIALS AND PROCESSES AND USES THEREOF

CROSS-REFERENCE TO RELATED APPLICATIONS

This application claims priority to U.S. Provisional Application Ser. No. 62/632,681 filed Feb. 20, 2018, which is herein incorporated by reference in its entirety.

TECHNICAL FIELD

This disclosure relates to materials designated as EMM-37, processes of making such materials, uses of these materials, structure directing agents (SDAs) employed in making such materials, and processes and intermediates used in making such structure directing agents.

BACKGROUND

Zeolites can be used as adsorbents and catalysts or support for catalysts for hydrocarbon conversions. Zeolites have uniform cavities and pores that are interconnected by channels. The sizes and dimensions of cavities and the pores allow for adsorption of molecules of certain sizes. Due to its ability to adsorb molecules through size selections, zeolites have many uses including hydrocarbon conversions, e.g., cracking, hydrocracking, disproportionation, alkylation, oligomerization, and isomerization.

Zeolites that find application in catalysis and adsorption include any of the naturally occurring or synthetic crystalline zeolites. Examples of these zeolites include large pore zeolites, intermediate pore size zeolites, and small pore zeolites. These zeolites and their isotypes are described in http://America.iza-structure.org/IZA-SC/ftc_table.php. A large pore zeolite generally has a pore size of at least about 7 Å and includes LTL, VFI, MAZ, FAU, OFF, *BEA, and MOR framework type zeolites (IUPAC Commission of Zeolite Nomenclature). Examples of large pore zeolites include mazzite, offretite, zeolite L, VPI-5, zeolite Y, zeolite X, omega, and Beta. An intermediate pore size zeolite generally has a pore size from about 5 Å to less than about 7 Å and includes, for example, MFI, MEL, EUO, MTT, MFS, AEL, AFO, HEU, FER, MWW, and TON frame-work type zeolites (IUPAC Commission of Zeolite Nomenclature). Examples of intermediate pore size zeolites include ZSM-5, ZSM-11, ZSM-22, MCM-22, silicalite 1, and silicalite 2. A small pore size zeolite has a pore size from about 3 Å to less than about 5.0 Å and includes, for example, CHA, ERI, KFI, LEV, SOD, and LTA framework type zeolites (IUPAC Commission of Zeolite Nomenclature). Examples of small pore zeolites include ZK-4, ZSM-2, SAP0-34, SAP0-35, ZK-14, SAP0-42, ZK-21, ZK-22, ZK-5, ZK-20, zeolite A, chabazite, zeolite T, gmelinite, ALPO-17, and clinoptilolite. However, there remains a desire for new zeolites.

SUMMARY

In one aspect, this disclosure provides EMM-37 materials, processes of preparing these materials, and uses thereof. This disclosure provides porous crystalline EMM-37 materials, where part or all of an SDA has been removed, having at least six X-ray diffraction (XRD) peaks in degree 2-theta selected from Table 1:

TABLE 1

| degree 2-theta (±0.20) | relative intensity [100 × I/(Io)] |
|---|---|
| 8.93 | 30-60 |
| 10.49 | 40-80 |
| 11.12 | 60-100 |
| 12.68 | 10-40 |
| 15.33 | 10-40 |
| 15.88 | 5-25 |
| 22.77 | 50-80 |
| 23.90 | 40-60 |
| 27.58 | 20-40 |

In a further aspect, provided herein is a crystalline EMM-37 material having a framework defined by the following connectivities in Table 2 for the tetrahedral (T) atoms in the unit cell, the tetrahedral (T) atoms being connected by bridging atoms:

TABLE 2

| T atom | Connected to: |
|---|---|
| T1 | T3, T5, T7, T9 |
| T2 | T5, T7, T8, T11 |
| T3 | T1, T4, T11, T12 |
| T4 | T3, T6, T9, T10 |
| T5 | T1, T2, T10, T13 |
| T6 | T4, T7, T12, T14 |
| T7 | T1, T2, T6, T13 |
| T8 | T2, T10, T12, T14 |
| T9 | T1, T4, T12, T14 |
| T10 | T4, T5, T8, T11 |
| T11 | T2, T3, T10, T13 |
| T12 | T3, T6, T8, T9 |
| T13 | T5, T7, T11, T14 |
| T14 | T6, T8, T9, T13 |

In another aspect, this disclosure provides a porous crystalline EMM-37 material, where part or all of an SDA has been removed, having a composition including Formula I:

$(m)X_2O_3{:}YO_2$  (Formula I), wherein $0.01 \leq m \leq 0.25$, X is a trivalent element, and Y is a tetravalent element. The EMM-37 materials may contain components other than the trivalent and tetravalent oxides of Formula I such as those described in the Detailed Description and Example sections.

In yet another aspect, provided herein is a crystalline EMM-37 material, in its as-made form, having at least six XRD peaks in degree 2-theta selected from Table 3:

TABLE 3

| degree 2-theta (±0.20) | relative intensity [100 × I/(Io)] |
|---|---|
| 8.73 | 20-40 |
| 10.37 | 20-60 |
| 11.04 | 60-100 |
| 12.56 | 20-40 |
| 17.52 | 30-70 |
| 19.45 | 30-70 |
| 20.47 | 30-70 |
| 22.40 | 50-80 |
| 23.83 | 20-60 |
| 27.18 | 30-70 |

In yet another aspect, provided herein is a crystalline EMM-37 material, in its as-made form, having a composition including Formula II:

$(n)G{:}(v)X_2O_3{:}YO_2$  (Formula II), wherein 0.01≤v≤0.25, 0.03≤n≤0.25, G is an organic structure directing agent, X is a trivalent element, and Y is a tetravalent element. The EMM-37 materials may contain components other than the trivalent and tetravalent oxides of Formula II such as those described in the Detailed Description and Example sections.

In still yet another aspect, this disclosure provides processes of preparing the materials described herein.

In a further aspect, provided herein is an SDA material comprising or being Compound H having the following structure:

(Compound H)

wherein A is an ion, and processes of preparing the same.

Any two or more of the features described in this specification, including in this summary section, can be combined to form combinations of features not specifically described herein. The details of one or more features are set forth in the accompanying drawings and the description below. Other features and advantages will be apparent from the description and drawings, and from the claims.

DETAILED DESCRIPTION

Provided herein are materials designated as EMM-37, processes of preparing these materials, uses thereof, structure directing agents for preparing EMM-37, processes and intermediates used in making such SDAs. The EMM-37 materials are crystalline and porous. The EMM-37 material, where part or all of the SDA has been removed (e.g., thermal treatment or other treatment to remove the structure directing agent (SDA) from the pores), may comprise of various components such as those described herein including a chemical composition of oxides of a trivalent element (e.g., $X_2O_3$) and oxides of a tetravalent element (e.g., $YO_2$), where these oxides can be in various molar ratios. X is a trivalent element and Y is a tetravalent element. The as-made EMM-37 (i.e., before thermal treatment or other treatment to remove the SDA from the pores) may include a SDA, one of the components of the synthesis mixture, within its pores. In one aspect, the as-made EMM-37 material may be subjected to thermal treatment or other treatment to remove part or all of the SDA. Thermal treatment (e.g., calcination) of the as-made EMM-37 material typically exposes the materials to high temperatures, e.g., to 400-700° C., in an atmosphere selected from air, nitrogen, or a mixture thereof in a furnace. In another aspect, ozone treatment of the as-made EMM-37 material may be used to remove part or all of the SDA. The EMM-37 material, where part or all of the SDA has been removed, can be used as adsorbents and catalysts or support for catalysts for hydrocarbon conversions, e.g., conversion of organic compounds to a converted product. EMM-37 described herein, which is a small pore zeolite, has the ability to separate small-molecules.

The EMM-37 material, where part of all of the SDA has been removed, has at least six XRD peaks in degree 2-theta selected from Table 1:

TABLE 1

| degree 2-theta (±0.20) | relative intensity [100 × I/(Io)] |
|---|---|
| 8.93 | 30-60 |
| 10.49 | 40-80 |
| 11.12 | 60-100 |
| 12.68 | 10-40 |
| 15.33 | 10-40 |
| 15.88 | 5-25 |
| 22.77 | 50-80 |
| 23.90 | 40-60 |
| 27.58 | 20-40 |

In one or more aspects, the EMM-37 material (where part or all of the SDA has been removed) may have at least six XRD peaks with the degree 2-theta and d-spacing values selected from Table 1A, wherein the d-spacing values have a deviation determined based on the corresponding deviation ±0.20 degree 2-theta when converted to the corresponding values for d-spacing using Bragg's law:

TABLE 1A

| degree 2-theta (±0.20) | d-spacing (Å) | relative intensity [100 × I/(Io)] |
|---|---|---|
| 8.93 | 9.90 | 30-60 |
| 10.49 | 8.42 | 40-80 |
| 11.12 | 7.95 | 60-100 |
| 12.68 | 6.98 | 10-40 |
| 15.33 | 5.77 | 10-40 |
| 15.88 | 5.58 | 5-25 |
| 22.77 | 3.90 | 50-80 |
| 23.90 | 3.72 | 40-60 |
| 27.58 | 3.23 | 20-40 |

The XRD patterns with the XRD peaks described herein use $Cu(K_\alpha)$ radiation. The EMM-37 material may have at least seven, at least eight, or nine XRD peaks selected from Table 1 or Table 1A.

The EMM-37 material (for example, with SDA or where part or all of the SDA is removed) has a framework defined by the connectivities in Table 2 for the tetrahedral (T) atoms in the unit cell, where the tetrahedral (T) atoms are connected by bridging atoms. The connectivities can be calculated by the computer algorithm zeoTsites, a Fortran code for topological and crystallographic tetrahedral sites analysis in zeolites and zeotypes. See e.g., G. Sastre, J. D. Gale, Microporous and Mesoporous Materials 2001, 43, pages 27-40. The tetrahedral atoms may include one or more elements selected from B, Al, Fe, Ga, Si, Ge, Sn, Ti, and Zr, or a mixture thereof. For example, the tetrahedral atoms may be selected from B, Al, or Si, or a mixture thereof. For example, the tetrahedral atoms may comprise or be Si or Al. The bridging atoms may be selected from O, N, and C, or a mixture thereof. The bridging atoms may comprise or be oxygen atoms (e.g., at least 50%, at least 60%, at least 70%, at least 80%, at least 90%, or at least 95% of the bridging atoms may be oxygen). The bridging atom C may be incorporated from the various components used to make the zeolite, e.g., the silica source. The bridging atom N may be incorporated into the zeolite after the SDA has been removed.

In one or more aspects, the EMM-37 material (where part or all of the SDA has been removed by thermal treatment or other treatments) may have a micropore volume of 0.10 to 0.28 cc/g, e.g., 0.20 to 0.28 cc/g. The micropore volume may be 0.10 to 0.20 (e.g., 0.12), or 0.20 to 0.25 (e.g., 0.21 or 0.22) cc/g. The EMM-37 material may have at least six, at least seven, at least eight, or nine XRD peaks selected from Table 1 or Table 1A; and a micropore volume of 0.10 to 0.28 cc/g, e.g., 0.20 to 0.28 cc/g.

In one or more other aspects, the EMM-37 material (where part or all of the SDA has been removed) may have five XRD peaks XRD peaks selected from Table 1B:

TABLE 1B

| degree 2-theta (±0.20) | relative intensity [100 × I/(Io)] |
| --- | --- |
| 8.93 | 30-60 |
| 10.49 | 40-80 |
| 11.12 | 60-100 |
| 22.77 | 50-80 |
| 23.90 | 40-60 | and a micropore volume of 0.10 to 0.28 cc/g.

The EMM-37 material (where part or all of the SDA has been removed) may have a composition that is optionally represented by Formula I:

$$(m)X_2O_3:YO_2$$ (Formula I), wherein 0.01≤m≤0.25, X is a trivalent element, and Y is a tetravalent element. X may be selected from B, Al, Fe, and Ga, or a mixture thereof. For example, X may comprise or be Al. Y may be selected from Si, Ge, Sn Ti, and Zr, or a mixture thereof. For example, Y may comprise or be Si. The oxygen atoms in Formula I may be replaced by carbon atoms (e.g., in the form of $CH_2$), which can come from sources of the components used to prepare the as-made EMM-37. The oxygen atoms in Formula I can also be replaced by nitrogen atoms, e.g., after the SDA has been removed. Formula I can represent the framework of a typical EMM-37 material, where part or all of the SDA has been removed, and is not meant to be the sole representation of an EMM-37 material. The EMM-37 material may contain SDA and/or impurities after appropriate treatments to remove the SDA and impurities, which are not accounted for in Formula I. Further, Formula I does not include the protons and charge compensating ions that may be present in the EMM-37 material.

The variable m represents the molar ratio relationship of $X_2O_3$ to $YO_2$ in Formula I. For example, when m is 0.01, the molar ratio of Y to X is 50 (e.g., the molar ratio of Si/Al is 50). When m is 0.25, the molar ratio of Y to X is 2 (e.g., the molar ratio of Si/Al is 2). The molar ratio of Y to X may be 5 to 40, 5 to 25, or 4 to 15 (e.g., the molar ratio of Si/Al is 5 to 40, 5 to 25, or 4 to 15). The molar ratio of Y to X may be 4, 5, 6, 7, 8, 9, 10, 11, or 12 (e.g., the molar ratio of Si/Al is 4, 5, 6, 7, 8, 9, 10, 11, or 12).

The as-made (e.g., without thermal treatment) EMM-37 material has at least six XRD peaks in degree 2-theta selected from Table 3:

TABLE 3

| degree 2-theta (±0.20) | relative intensity [100 × I/(Io)] |
| --- | --- |
| 8.73 | 20-40 |
| 10.37 | 20-60 |
| 11.04 | 60-100 |
| 12.56 | 20-40 |
| 17.52 | 30-70 |
| 19.45 | 30-70 |
| 20.47 | 30-70 |
| 22.40 | 50-80 |
| 23.83 | 20-60 |
| 27.18 | 30-70 |

In one or more aspects, the as-made (e.g., without treatment to remove the SDA) EMM-37 material may have at least six XRD peaks with the degree 2-theta and d-spacing values selected from Table 3A, wherein the d-spacing values have a deviation determined based on the corresponding deviation ±0.20 degree 2-theta when converted to the corresponding values for d-spacing using Bragg's law:

TABLE 3A

| degree 2-theta (±0.20) | d-spacing (Å) | relative intensity [100 × I/(Io)] |
| --- | --- | --- |
| 8.73 | 10.12 | 20-40 |
| 10.37 | 8.53 | 20-60 |
| 11.04 | 8.01 | 60-100 |
| 12.56 | 7.04 | 20-40 |
| 17.52 | 5.06 | 30-70 |
| 19.45 | 4.56 | 30-70 |
| 20.47 | 4.34 | 30-70 |
| 22.40 | 3.97 | 50-80 |
| 23.83 | 3.73 | 20-60 |
| 27.18 | 3.28 | 30-70 |

The as-made EMM-37 material may have at least seven, at least eight, at least nine, or ten XRD peaks selected from Table 3 or Table 3A.

In one or more aspects, the as-made EMM-37 material may be described as having a triclinic unit cell a-parameter of 8.8±0.3 Å, b-parameter of 9.6±0.3 Å, c-parameter of 10.7±0.3 Å, α of 104±6°, β of 100±6°, and γ of 100±6°. The as-made EMM-37 material may have at least six, at least seven, at least eight, at least nine, or ten XRD peaks selected from Table 3 or Table 3A; and a triclinic unit cell a-parameter of 8.8±0.3 Å, b-parameter of 9.6±0.3 Å, c-parameter of 10.7±0.3 Å, α of 104±6°, β of 100±6°, and γ of 100±6°.

In one or more other aspects, the as-made EMM-37 material may have six XRD peaks selected from Table 3B:

TABLE 3B

| degree 2-theta (±0.20) | relative intensity [100 × I/(Io)] |
| --- | --- |
| 8.73 | 20-40 |
| 10.37 | 20-60 |
| 11.04 | 60-100 |
| 17.52 | 30-70 |
| 19.45 | 30-70 |
| 22.40 | 50-80 | and a triclinic unit cell a-parameter of 8.8±0.3 Å, b-parameter of 9.6±0.3 Å, c-parameter of 10.7±0.3 Å, α of 104±6°, β of 100±6°, and γ of 100±6°.

Optionally, the as-made EMM-37 material may have a composition that is represented by Formula II:

$$(n)G:(v)X_2O_3:YO_2$$ (Formula II), wherein 0.01≤v≤0.25, 0.03≤n≤0.25, G is an organic structure directing agent, X is a trivalent element, and Y is a tetravalent element. X may be selected from B, Al, Fe, and Ga, or a mixture thereof. For example, X may comprise or be Al. Y may be selected from Si, Ge, Sn Ti, and Zr, or a mixture thereof. For example, Y may comprise or be Si. Formula II can represent the framework of a typical as-made EMM-37 material with SDA, and is not meant to be the sole representation of such material. The as-made EMM-37 material may contain impurities that are not represented by Formula II. Further, Formula II does not include the protons and charge compensating ions that may be present in the as-made EMM-37 material. Similar to Formula I, the oxygen atoms in Formula II may be replaced by carbon atoms (e.g., in the form of $CH_2$), which can come from sources of the components used to prepare the as-made EMM-37.

The variable v represents the molar ratio relationship of $X_2O_3$ to $YO_2$ in Formula II. For example, when v is 0.01, the molar ratio of Y to X is 50 (e.g., the molar ratio of Si/Al is 50). When v is 0.25, the molar ratio of Y to X is 2 (e.g., the molar ratio of Si/Al is 2). The molar ratio of Y to X may be 5 to 40, 5 to 25, or 4 to 15 (e.g., the molar ratio of Si/Al is 5 to 40, 5 to 25, or 4 to 15). The molar ratio of Y to X may be 4, 5, 6, 7, 8, 9, 10, 11, or 12 (e.g., the molar ratio of Si/Al is 4, 5, 6, 7, 8, 9, 10, 11, or 12).

The variable n represents the molar ratio relationship of organic structure directing agent G to $YO_2$ in Formula II. For example, when n is 0.03, the molar ratio of G to Y is 0.03. When n is 0.25, the molar ratio of G to Y is 0.25. The molar ratio of G to Y may be 0.05 to 0.15, 0.10 to 0.25, 0.15, or 0.25.

The process used to prepare the as-made EMM-37 materials may be described as follows:

(i) mixing a composition comprising a source of hydroxide ions, a source of an oxide of a tetravalent element Y, a source of a trivalent element X, and optionally a structure directing agent (G) comprising a bispyrrolidinium dication;
(ii) heating the mixed composition; and
(iii) isolating crystals of EMM-37 material.

The composition may have a molar ratio of $YO_2$ to $X_2O_3$ 2 to 50 (e.g., 5 to 30, 4 to 25 or 5 to 20). The composition may also have a molar ratio of $H_2O$ to $YO_2$ 1 to 50 (e.g., 10 to 40). The composition may also have a molar ratio of $OH^-$ to $YO_2$ 0.05 to 0.5 (e.g., 0.10 to 0.30). The composition may have a molar ratio of G to $YO_2$ 0.03 to 0.25 (e.g., 0.10 to 0.25).

Carbon in the form of $CH_2$ may be present in the various sources of components used to prepare EMM-37, e.g., tetravalent element source (silica source), and incorporated into the EMM-37 framework as bridging atoms. Nitrogen atoms may be incorporated into the framework of the EMM-37 material as bridging atoms after the SDA has been removed.

In one or more other aspects, the as-made EMM-37 material may be prepared by initially mixing a trivalent element X source with a hydroxide solution of SDA, and then subsequently adding a tetravalent Y source to the mixture to form a base mixture of the components. Optionally, seeds of an EMM-37 material may be added to the base mixture. In one or more aspects, the mixture after solvent adjustment (e.g., where the desired water to silica ratio is achieved) may be mixed by a mechanical process such as stirring or high shear blending to assure suitable homogenization of the base mixture, for example, using dual asymmetric centrifugal mixing (e.g., a FlackTek speedmixer) with a mixing speed of 1000 to 3000 rpm (e.g., 2000 rpm).

Depending on the nature of the components in the base mixture, an amount of solvent (e.g., water from the hydroxide solution, and optionally methanol and ethanol from the hydrolysis of silica sources) of the base mixture may be removed such that a desired solvent to $YO_2$ molar ratio is achieved for the resulting mixture. Suitable methods for reducing the solvent content may include evaporation under a static or flowing atmosphere such as ambient air, dry nitrogen, dry air, or by spray drying or freeze drying. Water may be added to the resulting mixture to achieve a desired $H_2O/YO_2$ molar ratio when too much water is removed during the solvent removal process. In some examples, water removal is not necessary when the preparation have sufficient $H_2O/YO_2$ molar ratio.

The mixed mixture is then subject to crystallization conditions suitable for the EMM-37 material to form. Crystallization of an EMM-37 material may be carried out under static or stirred conditions in a suitable reactor vessel, such as for example, polypropylene jars or Teflon lined or stainless steel autoclaves placed in a convection oven maintained at a temperature of about 100 to about 200° C. for a period of time sufficient for crystallization to occur, e.g., from about 1 day to about 30 days (e.g., 1 day to 1 to 14 days, or 1 day to 7 days). Thereafter, the solid crystals of the as-made EMM-37 material are separated from the liquid (e.g., by filtration or centrifugation) and recovered.

Examples of sources of the tetravalent element Y may be selected from colloidal suspensions of silica, precipitated silica, fumed silica, alkali metal silicates, tetraalkyl orthosilicates (e.g., tetraethyl orthosilicates, tetramethyl orthosilicates, etc.), and germanium oxide, or a mixture thereof. Other examples of sources of silica may include LUDOX® (e.g., LUDOX® LS-30, LUDOX® AS-40) colloidal silica, ULTRASIL® precipitated silica, CARBOSPERSE™, fumed silica suspension, or a mixture thereof.

The trivalent element X may comprise or be aluminum. Suitable sources of aluminum may be selected from metakaolin, alkali metal aluminates, aluminum alkoxides, and water-soluble aluminum salts, such as aluminum nitrate, or a mixture thereof. Additionally or alternatively, trivalent element X may comprise or be boron. Suitable sources of boron may be selected from boric acid, sodium teraborate, and potassium tetraborate, or a mixture thereof.

Part or all of the SDA incorporated into the pores during the synthesis of an as-made EMM-37 material may be removed to form the thermally-treated EMM-37 material. Removal of SDA may be carried out using thermal treatment (e.g., calcination) in which the as-made EMM-37 material is heated in an atmosphere selected from air, nitrogen, or a mixture thereof at a temperature sufficient to remove part or all of the SDA. While subatmospheric pressure may be employed for the thermal treatment, atmospheric pressure is desired for reasons of convenience. The thermal treatment may be performed at a temperature up to 700° C. e.g., 400° C. to 700° C. The temperature measured is the temperature of the surrounding environment of the sample. The thermal treatment (e.g., calcination) may be carried out in a box furnace in dry air, which has to been exposed to a drying tube containing drying agents that remove water from the air. The heating may be carried out for 1 day to 14 days at 400° C. to 700° C. (e.g., 515 or 540° C.). The heating may first be carried out under a nitrogen atmosphere up to 400° C. and then the atmosphere may be switched to air at 400° C.

The as-made EMM-37 material may include a structure directing agent, e.g., a bispyrrolidinium dication. Alternative methods of synthesizing the porous crystalline EMM-37 material may be carried out without the use of an SDA. Suitable sources of the structure directing agents may be selected from the hydroxides and/or salts of the relevant diquaternary ammonium compounds. For example, the structure directing agent may comprise or be Compound H having the following structure:

(Compound H)

wherein A is an ion.

For example, A may be a tosylate, OH (hydroxyl), or halide, such as I or Br. In one or more aspects, A may comprise or be a hydroxyl group (OH). Compound H has two stereocenters and, thus, Compound H has RS, SS or RR configurations. For example, Compound H may comprise or be an RS configuration. The SDA used in the preparation of the as-made EMM-37 material may be Compound H having an RS configuration.

The process of preparing Compound H or a specific stereoisomer thereof may comprise:

(i) converting Compound 1:

Compound 1 to Compound 2:

Compound 2

(ii) converting Compound 2 to Compound 3:

Compound 3

(iii) converting Compound 3 to Compound H:

Compound H and (iv) optionally purifying Compound H to the desired stereoisomer (e.g., the RS isomer).

Compound 2 may be prepared by converting Compound 1 to Compound 2. For example, Compound 1 may be reacted with methylamine and methanol in the presence of a solvent. The solvent may comprise or be a protic solvent, such as water. The amount of methylamine used may be 1 to 3 molar equivalents (e.g., 1.6 molar equivalents) of the methylamine based on 1 molar equivalent of Compound 1. The conversion of Compound 1 to Compound 2 may include microwaving Compound 1 with methylamine. The microwaving may be at a temperature of 150° C. to 170° C. (e.g., heating the reaction mixture in a sealed vessel to a temperature of 150° C. to 170° C.). The microwaving may include a 15-minute ramp to 150° C. to 170° C. (e.g., 160° C.) and maintaining the temperature 150° C. to 170° C. (e.g., 160° C.) for 1 to 3 hours (e.g., 1 hour).

Compound 3 may be prepared by converting Compound 2 to Compound 3. The conversion of Compound 2 to Compound 3 may include reacting Compound 2 with a reducing agent in the presence of a solvent. For example, the reducing agent may comprise or be lithium aluminum hydride (LAH). The amount of reducing agent used may be 2 to 5 molar equivalents (e.g., 3 to 4 or 3.5 molar equivalents) of the reducing agent based on 1 molar equivalent of Compound 2. The solvent may comprise or be an ether, such as tetrahydrofuran (THF).

Compound H may be prepared by converting Compound 3 to Compound H. For example, Compound 3 may be reacted with a halo alkane source in the presence of a solvent. The halo alkane source may comprise or be an iodide source, such as iodomethane. The amount of halo alkane source used may be 2 to 4 molar equivalents (e.g., 3 molar equivalents) of the halo alkane source based on 1 molar equivalent of Compound 3. The solvent may comprise or be a protic solvent, such as methanol.

Compound H may optionally be purified to obtain the desired stereoisomer, e.g., SS, RR, or RS. For example, Compound H may be obtained as substantially pure as the RS stereoisomer. "Substantially pure" with respect to Compound H means at least 80%, 90%, 95%, 96%, 97%, 98%, or 99% pure as the SS, RR, or RS stereoisomer. The purification may include precipitating the desired stereoisomer (e.g., RS stereoisomer) from a solvent or a mixture of one or more solvents. The solvent may comprise or be a protic solvent. For example, the protic solvent may be selected from methanol, water, or a mixture thereof. For example, the Compound H may be dissolved in hot methanol (e.g. methanol at a temperature higher than room temperature), and deionized water may be added to the Compound H methanol solution to precipitate or crystallize Compound H. Using methanol/water mixture as the solvent system to crystallize or precipitate Compound H, the RS isomer can be isolated first as a solid (e.g., crystals or precipitate) and the remaining isomers can subsequently be isolated from the residual solution by removing the solvents, e.g., in vacuo. The RS isomer may be separated from the RR and SS isomers as described above. The RR and SS enantiomers may be separated from each other by chiral separating agents.

The anions of Compound H may be converted to other anions. For example, the anion iodide may be converted to the hydroxide anion by standard methods known to those of ordinary skill in the art, e.g., resin exchange.

General Features

EMM-37 materials (where part or all of the SDA is removed) may be combined with a hydrogenating component. The hydrogenating component may be selected from molybdenum, tungsten, rhenium, nickel, cobalt, chromium, manganese, or a noble metal, such as platinum or palladium where a hydrogenation-dehydrogenation function is to be performed. Such hydrogenating components may be incorporated into the composition by way of one or more of the following processes: cocrystallizing; exchanging into the composition to the extent a Group IIIA element, e.g., aluminum, is in the structure; impregnating therein or physically admixing therewith. In one or more aspects, such hydrogenating components may be impregnated into the EMM-37 material. In the case of platinum, the EMM-37 materials may be impregnated with a solution containing a platinum metal-containing ion. Suitable platinum compounds for impregnating may be selected from chloroplatinic acid, platinous chloride, and compounds containing a platinum amine complex.

EMM-37 materials (where part or all of the SDA is removed), when employed either as an adsorbent or as a catalyst, may be dehydrated, at least partially. Such dehydration may be accomplished by heating to a temperature in the range of 200 to 370° C. (e.g., temperature of the surrounding environment of the sample) in an atmosphere selected from air, nitrogen, or a mixture thereof, and at atmospheric, subatmospheric or superatmospheric pressures for between 30 minutes and 48 hours. Dehydration may also be performed at room temperature by placing the EMM-37 materials in a vacuum; however, a longer period of time is required to obtain a sufficient amount of dehydration.

EMM-37 materials (where part or all of the SDA is removed) may be used as an adsorbent or in an aluminosilicate form, as a catalyst to catalyze a wide variety of organic compound conversion processes. Examples of chemical conversion processes, which are effectively catalyzed by the modified EMM-37 materials described herein, either alone or in combination with one or more other catalytically active substances (including other crystalline catalysts), include those requiring a catalyst with acid activity. Examples of organic conversion processes, which may be catalyzed by the modified EMM-37 materials described herein include cracking, hydrocracking, disproportionation, alkylation, oligomerization, and isomerization.

EMM-37 materials (where part or all of the SDA is removed) may be incorporated with another material resistant to the temperatures and other conditions employed in organic conversion processes. Such resistant materials may be selected from active materials, inactive materials, synthetic zeolites, naturally occurring zeolites, inorganic materials or a mixture thereof. Examples of such resistant materials may be selected from clays, silica, metal oxides such as alumina, or a mixture thereof. The inorganic material may be either naturally occurring, or in the form of gelatinous precipitates or gels, including mixtures of silica and metal oxides. Use of a resistant material in conjunction with an EMM-37 material, i.e., combined therewith or present during synthesis of the as-made EMM-37 crystal, which crystal is active, tends to change the conversion and/or selectivity of the catalyst in certain organic conversion processes. Inactive resistant materials suitably serve as diluents to control the amount of conversion in a given process so that products can be obtained in an economic and orderly manner without employing other means for controlling the rate of reaction. These materials may be incorporated into naturally occurring clays, e.g., bentonite and kaolin, to improve the crush strength of the catalyst under commercial operating conditions. Said inactive resistant materials, i.e., clays, oxides, etc., function as binders for the catalyst. A catalyst having good crush strength can be beneficial because in commercial use, it is desirable to prevent the catalyst from breaking down into powder-like materials.

Naturally occurring clays which may be composited with EMM-37 materials include the montmorillonite and kaolin family, which families include the subbentonites, and the kaolins commonly known as Dixie, McNamee, Ga. and Florida clays or others in which the main mineral constituent is halloysite, kaolinite, dickite, nacrite, or anauxite. Such clays may be used in the raw state as originally mined or initially subjected to calcination, acid treatment or chemical modification. Binders useful for compositing with EMM-37 materials also include inorganic oxides selected from silica, zirconia, titania, magnesia, beryllia, alumina, or a mixture thereof.

EMM-37 materials (e.g., the as-made or calcined, or any other EMM-37 materials) may be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia, and silica-magnesia-zirconia.

The relative proportions of EMM-37 material and inorganic oxide matrix may vary widely, with the EMM-37 material content ranging from about 1 to about 90 percent by weight, of the composite or, when the composite is prepared in the form of beads, in the range of about 2 to about 80 weight percent of the composite.

As used herein, and unless otherwise specified, a numeric value or range of values may deviate to an extent deemed reasonable to one of ordinary skill in the relevant art. It is well known that instrument variation and other factors can affect the numerical values. Such deviation, unless otherwise specified, may be plus or minus 2%, 5%, 10%, or 15% of the numeric value or range of values indicated.

The EMM-37 materials described herein may be at least 50%, at least 60%, at least 70%, at least 80%, at least 90%, at least 95%, at least 97%, or at least 99% (e.g., 99.5% or 99.9%) by weight pure EMM-37 material, based on the total weight of the composition, by quantification using XRD or NMR spectroscopy (e.g., by measuring the area or the relative intensity of the relevant peaks), or by other known methods appropriate for such determination. The remainder of the material is non-EMM-37 material, which may be structure directing agent, amorphous material, other impurities, or a mixture thereof.

The EMM-37 material described herein is substantially crystalline. As used herein, the term "crystalline" refers to a crystalline solid form of a material, including, but not limited to, a single-component or multiple-component crystal form, e.g., including solvates, hydrates, and a co-crystal. Crystalline can mean having a regularly repeating and/or ordered arrangement of molecules, and possessing a distinguishable crystal lattice. For example, crystalline EMM-37 can have different water or solvent content. The different crystalline lattices can be identified by solid state characterization methods such as by XRD (e.g., powder XRD). Other characterization methods known to a person of ordinary skill in the relevant art can further help identify the crystalline form as well as help determine stability and solvent/water content.

As used herein, the term "substantially crystalline" means a majority (greater than 50 wt %) of the weight of a sample of a material described is crystalline and the remainder of the sample is a non-crystalline form. In one or more aspects, a substantially crystalline sample has at least 95% crystallinity (e.g., 5% of the non-crystalline form), at least 96% crystallinity (e.g., 4% of the non-crystalline form), at least 97% crystallinity (e.g., 3% of the non-crystalline form), at least 98% crystallinity (e.g., about 2% of the non-crystalline form), at least 99% crystallinity (e.g., 1% of the non-crystalline form), and 100% crystallinity (e.g., 0% of the non-crystalline form).

The micropore volume of the EMM-37 materials described herein can be determined using methods known in the relevant art. For example, the materials can be measured with nitrogen physisorption, and the data can be analyzed by the t-plot method described in Lippens, B. C. et al., "Studies on pore system in catalysts: V. The t method", J. Catal., 4, 319 (1965), which describes micropore volume method and is incorporated herein by reference.

Figure 1:
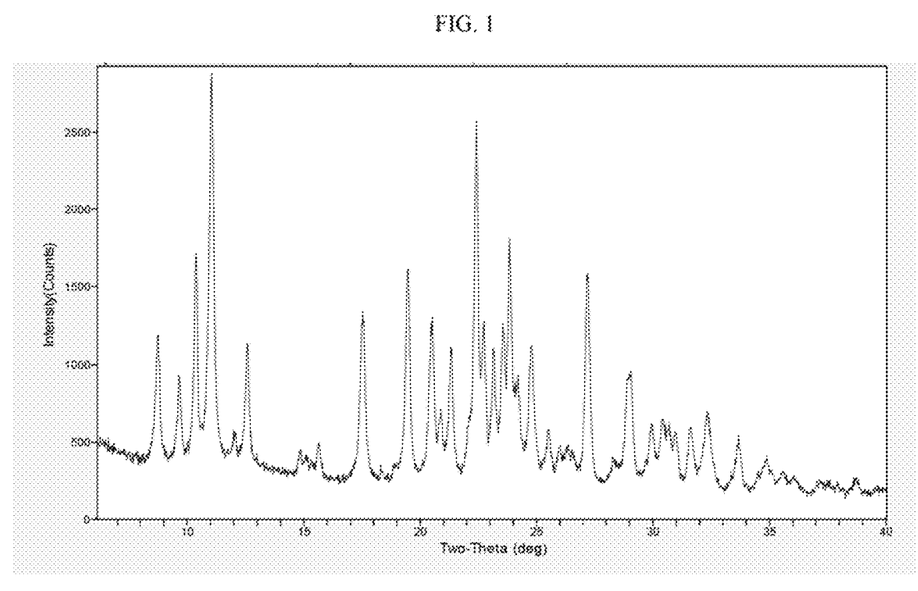
FIG. 1 shows a powder XRD pattern of an as-made EMM-37 material.
Figure 2:
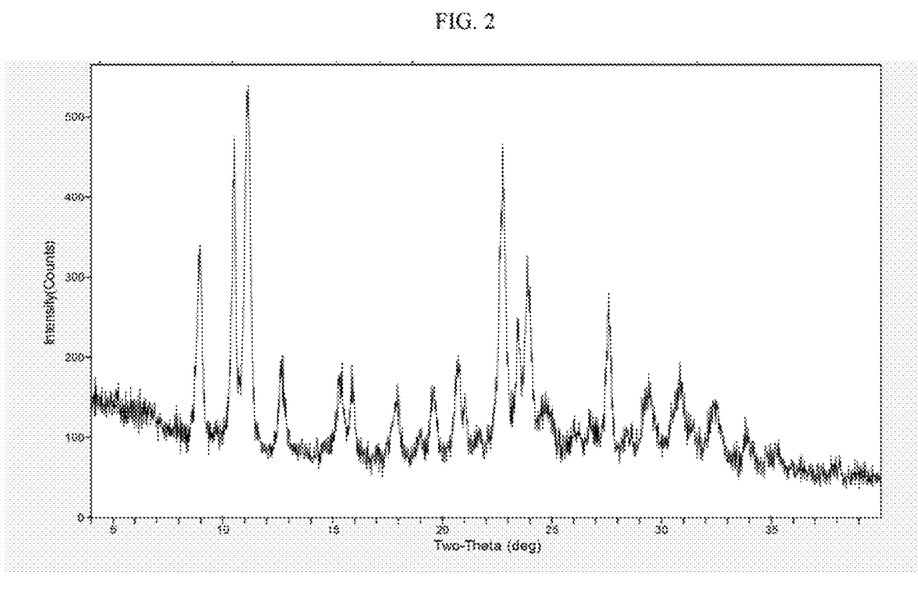
FIG. 2 shows powder XRD patterns of thermally-treated EMM-37 material calcined to 515° C.

The X-ray diffraction data reported herein were collected with a Bruker D4 Endeavor instrument in continuous mode using Cu Kα radiation with a step size of 0.01796° with the VANTEC-1 gaseous detector with 50 mm×16 mm active area. FIGS. 1 and 2 were collected at an effective count time of 278 sec/step and FIG. 3 at 347.5 sec/step. The interplanar spacings, d-spacings, were calculated in Angstrom units, and the relative intensities of the lines, I/I$_o$ is the ratio of the peak intensity to that of the intensity of the strongest line, above background. The intensities are uncorrected for Lorentz and polarization effects. The location of the diffraction peaks in 2-theta, and the relative peak area intensities of the lines, I/I(o), where I$_o$ is the intensity of the strongest line, above background, were determined with the MDI Jade peak search algorithm. It should be understood that diffraction data listed as single lines may consist of multiple overlapping lines which under certain conditions, such as differences in crystallographic changes, may appear as resolved or partially resolved lines. Typically, crystallographic changes can include minor changes in unit cell parameters and/or a change in crystal symmetry, without a change in the structure. These minor effects, including changes in relative intensities, can also occur as a result of differences in cation content, framework composition, nature and degree of pore filling, crystal size and shape, preferred orientation and thermal and/or hydrothermal history.

Aspects of the disclosure are described in greater detail by way of specific examples. The following examples are offered for illustrative purposes, and are not intended to limit the disclosure in any manner. Those of skill in the relevant art will readily recognize a variety of parameters can be changed or modified to yield essentially the same results.

EXAMPLES

Example 1: Synthesis of Compound H

Compound H was prepared according to Scheme 1.

Scheme 1

Compound 1

Step 1. 1,1'-dimethyl-[3,3'-bipyrrolidine]-2,2',5,5'-tetraone (Compound 2)

1.6 equivalent methylamine was reacted with 1 equivalent of the dianhydride 1,1-dimethyl-3,3'-bipyrrolidine-2,2',5,5'-tetraone in a microwave by using a 15-minute ramp to 160° C. and maintaining the temperature at 160° C. for 1 hour. Water was used as the solvent. After microwaving, the reaction mixture was dripped into a methanol solution comprising ~10 mL MeOH/1g mesobutane-1,2,3,4-tetracarboxylic anhydride. After 5-10 min, a white solid precipitated out of the solution. This solid was isolated on a frit and oven-dried. The white crystalline solid (56% yield) was pure Compound 2 as determined by $^1$H NMR.

Step 2. 1,1'-dimethyl-3,3'-bipyrrolidine (Compound 3)

A 3-necked 3000-ml round-bottom flask was equipped with an overhead stirrer and reflux condenser. 1500 mL tetrahydrofuran was then added to the flask. 16.89 g of Lithium aluminum hydride (LAH) in pellet form was then added and the suspension was mixed vigorously overnight. An ice bath was then placed around the flask. Next, 31.56 g 1,1'-dimethyl-[3,3'-bipyrrolidine]-2,2',5,5'-tetraone (Compound 2) was added gradually to the stirring mixture in 5-g increments over the course of about 2 hours. The mixture was then allowed to stir overnight. The following morning a heating mantle was placed underneath the flask, and the suspension was then refluxed for 2 hours. The flask was then cooled in an ice bath and about 400 ml diethyl ether was added to the mixture. At this point 200 mL of 45% NaOH solution was then added dropwise under vigorous stirring. After the grey solids became white, the solids were removed by filtration and the THF/ether layer was isolated using a separatory funnel. The solution was then dried with anhydrous magnesium sulfate and the solids were then removed by filtration. The diamine (Compound 3) was then recovered by rotoevaporation to obtain 63% yield of product. This procedure was repeated to make larger quantities of the diamine (Compound 3). NMR and $^{13}$C NMR indicated that the product to be about a 60/40 mixture of the two isomers.

Step 3. 1,1,1',1'-tetramethyl-[3,3'-bipyrrolidine]-1,1'-diium iodide (Compound H, where A is iodide)

51.92 g of the diamine (Compound 3) was added to 300 mL methanol. Next, 132 g iodomethane was added dropwise to the mixture with vigorous stirring. The next day, the solid precipitate was isolated by filtration. $^1$H and $^{13}$C NMR showed the product to be ~95% isomer A. The rest of the product was isolated by rotoevaporation of the solvent. The solid residues from the rotoevaporation were washed with acetone and then dried overnight. $^1$H and $^{13}$C NMR showed the product recovered from the solvent to be about 92% isomer B. The initially recovered solids were further purified by performing two recrystallizations from hot methanol with minimal addition of deionized water. From the recrystallization, large crystals were obtained that were used for a structure solution from single crystal X-ray diffraction. 47 g of the isomer A and 33 g of the isomer B were obtained. A single crystal structure solution showed that isomer A was the RS diastereomer. Isomer B was the RR and SS enantiomers, and these enantiomers were not separated from each other.

Isomer A: $^1$H NMR, 400 MHz, D$_2$O, aqueous solution: 1.75 (m, 2H), 2.20 (m, 2H), 2.58 (m, 2H), 2.94 (s, 6H), 3.02 (s, 6H), 3.13 (m, 2H), 3.43 (t, 4H), 3.64 (m, 2H); and $^{13}$C NMR, 100 MHz, D$_2$O, aqueous solution: 27.2, 39.8, 52.3, 53.3, 65.70, 68.9.

Isomer B: $^1$H NMR: 400 MHz, D$_2$O, aqueous solution: 1.94 (m, 2H), 2.38 (m, 2H), 2.66 (m, 2H), 3.01 (s, 6H), 3.10 (s, 6H), 3.10 (m, 2H), 3.51 (t, 4H), 3.61 (m, 2H); and $^{13}$C NMR, 100 MHz, D$_2$O, aqueous solution: 27.1, 39.6, 52.2, 53.3, 65.5, 68.6. (s represents singlet, t represents triplet, and m represents multiplet.)

Conversion of Compound H Iodide to Hydroxide Form

Isomer A was converted into its hydroxide form by dissolving it in water and adding it to 700 mL of Dowex LC NG hydroxide. The next day the resin was removed by filtration and washed with deionized water to remove the product from the resin. The aqueous fractions were then combined and concentrated under reduced pressure at about 60° C. The hydroxide concentration of this aqueous solution was 1.86 mmol OH-/g as determined by titration with a standard solution of 0.1 N HCl.

Example 2. Synthesis of as-Made EMM-37

In the syntheses below for Experiments 1-11, metakaolin was used as the aluminum source. Compound H from Example 1 was mixed with metakaolin, NaOH, deionized water, and LUDOX® AS-40. The Teflon liner was then capped and sealed inside a steel Parr autoclave. The autoclave was then heated under tumbling conditions in a convection oven maintained at 160° C. for 7-14 days. The products were isolated by centrifugation, resuspension in deionized water, and then another centrifugation. This process was repeated three times and the samples were collected for powder XRD.

The molar ratios and conditions used for the syntheses of Experiments 1-11 below included the following:

Experiment 1

Si/Al=5, NaOH/Si=0.30, SDA(OH)$_2$/Si=0.15 (isomer A), and H$_2$O/Si=30. After 14 days of heating at 160° C., the product was a mixture of EMM-37 and analcime as determined by XRD (approximately 50% of each phase). Experiment 1 was repeated (Experiment 1A) but with the molar ratio of Si/Al increased to 6.7. The product was EMM-37 with trace amounts of analcime (approximately 5-10%).

Experiment 2

Si/Al=10, NaOH/Si=0.30, SDA(OH)$_2$/Si=0.15 (isomer A) and H$_2$O/Si=31. After 28 days of heating at 160° C., the product was a mixture of EMM-37 and minor beta (approximately less than 25%) as determined by XRD.

Experiment 3

Si/Al=10, NaOH/Si=0.30, SDA(OH)$_2$/Si=0.15 (isomer A) and H$_2$O/Si=30 for 14 days at 160° C. Product was pure EMM-37 as determined by XRD. Experiment 3 was repeated (Experiment 3A) but with heating at 7 days for 160° C. The product was also pure EMM-37 as determined by XRD. Experiment 3 was additionally repeated (Experiment 3B) but with isomer B for the SDA. The product obtained was Nu-87 as determined by XRD.

Experiment 4

Si/Al=8, NaOH/Si=0.30, SDA(OH)$_2$/Si=0.15 (isomer A) and H$_2$O/Si=30 for 14 days at 160° C. The product was pure EMM-37 as determined by XRD.

Experiment 5

Si/Al=12, NaOH/Si=0.30, SDA(OH)$_2$/Si=0.15 (isomer A) and H$_2$O/Si=30 for 14 days at 160° C. The product was pure EMM-37 as determined by XRD. Experiment 5 was repeated (Experiment 5A) except with heating for 7 days at 160° C. The product was also pure EMM-37 as determined by XRD.

Experiment 6

Si/Al=10, NaOH/Si=0.10, SDA(OH)$_2$/Si=0.25 (isomer A) and H$_2$O/Si=30 for 14 days at 160° C. The product was EMM-37 with trace zeolite beta as determined by XRD.

Experiment 7

Si/Al=8, NaOH/Si=0.10, SDA(OH)$_2$/Si=0.25 and H$_2$O/Si=30 for 14 days at 160° C. Product was EMM-37 with minor sodalite.

Experiment 8

Si/Al=10, NaOH/Si=0.15, SDA(OH)$_2$/Si=0.225 (isomer A) and H$_2$O/Si=30 for 14 days at 160° C. The product was EMM-37 with minor sodalite as determined by XRD. Experiment 8 was repeated (Experiment 8A) except the Si/Al ratio was decreased to 8. The product was again EMM-37 and minor sodalite as determined by XRD.

Experiment 9

Si/Al=5, NaOH/Si=0.10, SDA(OH)$_2$/Si=0.25 (isomer A) and H$_2$O/Si=30 for 14 days at 160° C. The product was EMM-37 and minor sodalite as determined by XRD.

Experiment 10

Si/Al=6.7, NaOH/Si=0.10, SDA(OH)$_2$/Si=0.25 (isomer A) and H$_2$O/Si=30 for 14 days at 160° C. The product was a mixture of EMM-37 and analcime (approximately 50% of each phase) as determined by XRD.

Experiment 11

Si/Al=6.7, NaOH/Si=0.30, SDA(OH)$_2$/Si=0.15 and H$_2$O/Si=30 for 7 days at 160° C. The product was pure EMM-37 as determined by XRD. Experiment 11 was repeated (Experiment 11A) except with heating at 7 days for 160° C. The product was also EMM-37 with minor amorphous material as determined by XRD.

Example 3. Additional Syntheses of as-Made EMM-37

In a 23-mL Teflon liner, 2.65 g of the Compound H hydroxide solution (isomer A) ([OH—]=1.86 mmol/g) was mixed with 0.93 g metakaolin, 0.40 g 50% NaOH, 5.67 g deionized water, and 2.24 g LUDOX® AS-40, to which mixture 0.053 g EMM-37 seeds were added. The Teflon liner was then capped and sealed inside a 23-mL steel Parr autoclave. The autoclave was then heated under tumbling conditions (~40 rpm) in a convection oven maintained at 160° C. for 7 days. The product was then recovered by filtration and washed with about 250 mL deionized water. Powder XRD (FIG. 1) showed the product to be pure EMM-37 in its as-made form. The powder pattern could be indexed in a triclinic cell with a=8.82, b=9.63, c=10.65 Å and a=104.4, β=99.9, γ=99.5°. Table 4 shows the list of peaks and intensities for the as-made zeolite. TGA in air showed about 21.5% mass loss between 225 and 700° C.

TABLE 4

| degree 2-theta | d-spacing (Å) | relative intensity [100 × I/(Io)] |
|---|---|---|
| 8.73 | 10.12 | 29 |
| 9.66 | 9.15 | 17 |
| 10.37 | 8.53 | 39 |
| 11.04 | 8.01 | 100 |
| 12.02 | 7.36 | 6 |
| 12.56 | 7.04 | 28 |
| 14.82 | 5.97 | 4 |
| 15.08 | 5.87 | 3 |
| 15.32 | 5.78 | 3 |
| 15.63 | 5.67 | 9 |
| 17.52 | 5.06 | 51 |
| 18.34 | 4.83 | 1 |
| 18.96 | 4.68 | 4 |
| 19.45 | 4.56 | 52 |
| 20.47 | 4.34 | 45 |
| 20.86 | 4.25 | 13 |
| 21.30 | 4.17 | 31 |
| 22.15 | 4.01 | 14 |
| 22.40 | 3.97 | 65 |
| 22.72 | 3.91 | 31 |
| 23.14 | 3.84 | 28 |
| 23.31 | 3.81 | 1 |
| 23.55 | 3.77 | 30 |
| 23.83 | 3.73 | 39 |
| 24.08 | 3.69 | 22 |
| 24.22 | 3.67 | 9 |
| 24.76 | 3.59 | 41 |
| 13.60 | 6.51 | 4 |
| 25.49 | 3.49 | 14 |
| 25.96 | 3.43 | 5 |
| 26.28 | 3.39 | 5 |
| 26.57 | 3.35 | 8 |
| 26.53 | 3.36 | 3 |
| 27.18 | 3.28 | 50 |
| 28.28 | 3.15 | 4 |
| 28.46 | 3.13 | 3 |
| 28.90 | 3.09 | 28 |
| 29.06 | 3.07 | 14 |
| 29.68 | 3.01 | 1 |
| 29.93 | 2.98 | 18 |
| 30.40 | 2.94 | 22 |
| 30.67 | 2.91 | 9 |
| 30.96 | 2.89 | 10 |
| 31.60 | 2.83 | 19 |
| 32.31 | 2.77 | 30 |
| 33.37 | 2.68 | 2 |
| 33.65 | 2.66 | 12 |
| 34.49 | 2.60 | 5 |
| 34.68 | 2.58 | 2 |
| 34.86 | 2.57 | 6 |
| 35.09 | 2.56 | 4 |
| 35.52 | 2.53 | 6 |
| 36.03 | 2.49 | 7 |

When the procedure was repeated using the same molar ratios except that aluminum hydroxide was used as the aluminum source, zeolite beta was the product.

Example 4. Thermally-Treated EMM-37

An experiment was repeated as in Example 3 except the reactant quantities were scaled by a factor of 2.7. Powder XRD showed the product to be pure EMM-37. The sample was calcined in a muffle furnace by ramping the temperature to 400° C. at 2° C./min under nitrogen, and then ramping the temperature to 515, 540, or 600° C. in air at 2° C./min. The temperature was held at 515, 540, or 600° C. for 2 hours before each sample was allowed to cool to ambient temperature.

Figure 3:
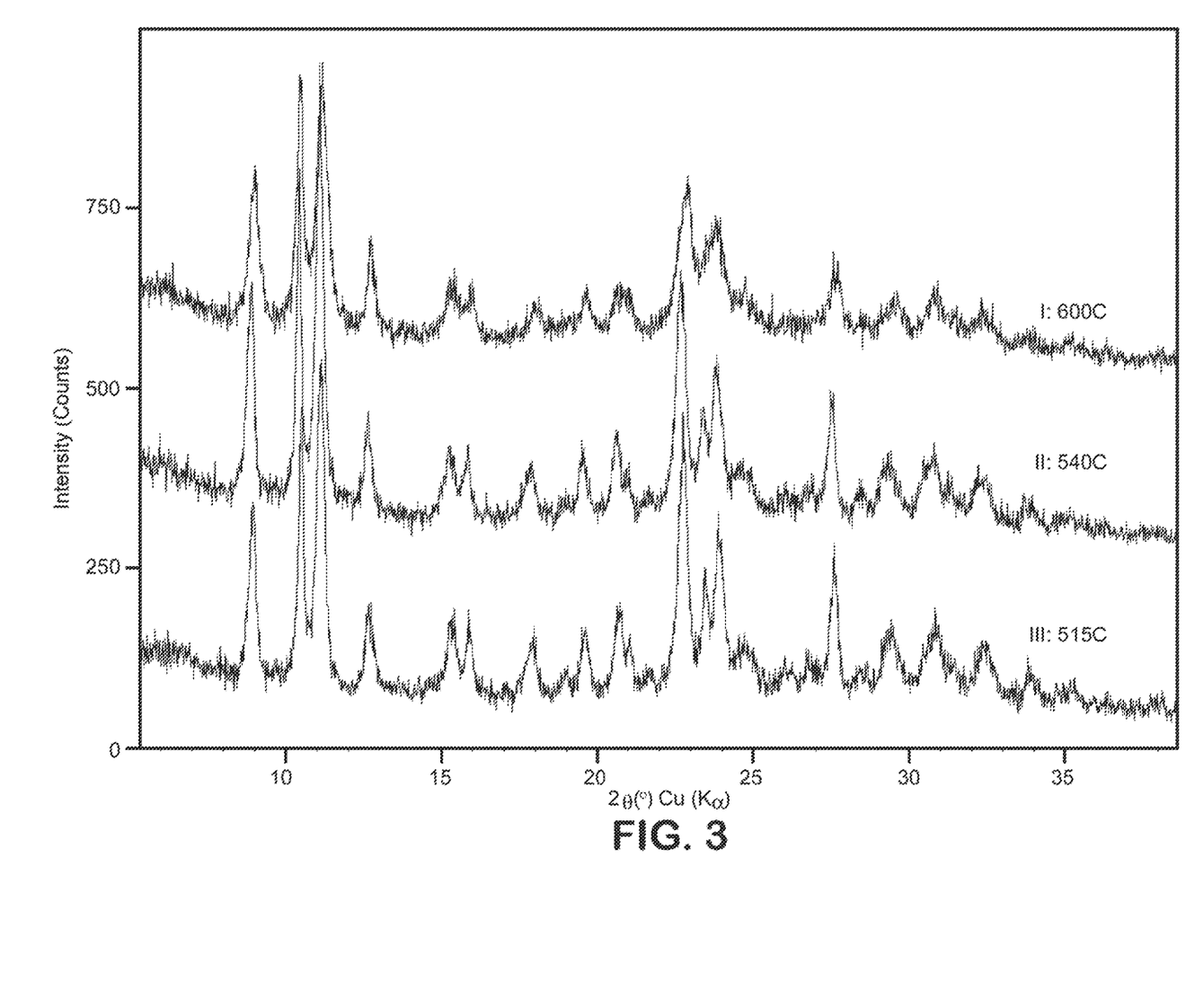
FIG. 3 shows powder XRD patterns of thermally-treated EMM-37 material calcined to 515° C., 540° C., and 600° C.

FIG. 3 shows that the powder XRD patterns of EMM-37 calcined to 515° C. (pattern III), 540° C. pattern (II), and 600° C. (pattern I). FIG. 3 shows that the XRD patterns broaden significantly after calcination to remove the organic structure directing agent (Compound H as isomer A). The degree of broadening increases from 515 to 600° C. Table 5 and FIG. 2 show the powder XRD pattern for the sample calcined at 515° C. The sample calcined to 515° C. had an adsorption capacity of 0.22 cc/g.

TABLE 5

| degree 2-theta | d-spacing (Å) | relative intensity [100 × I/(Io)] |
|---|---|---|
| 8.93 | 9.90 | 47 |
| 10.49 | 8.42 | 64 |
| 11.12 | 7.95 | 100 |
| 12.68 | 6.98 | 26 |
| 15.33 | 5.77 | 29 |
| 15.88 | 5.58 | 13 |
| 17.86 | 4.96 | 18 |
| 18.96 | 4.68 | 5 |
| 19.58 | 4.53 | 16 |
| 20.69 | 4.29 | 28 |
| 21.04 | 4.22 | 7 |
| 21.65 | 4.10 | 2 |
| 22.62 | 3.93 | 23 |
| 22.77 | 3.90 | 67 |
| 23.45 | 3.79 | 24 |
| 23.90 | 3.72 | 53 |
| 24.73 | 3.60 | 19 |
| 26.00 | 3.42 | 3 |
| 26.72 | 3.33 | 2 |
| 26.95 | 3.31 | 8 |
| 27.58 | 3.23 | 28 |
| 28.42 | 3.14 | 4 |
| 29.38 | 3.04 | 24 |
| 26.21 | 3.40 | 2 |

TABLE 5-continued

| degree 2-theta | d-spacing (Å) | relative intensity [100 × I/(Io)] |
|---|---|---|
| 30.79 | 2.90 | 41 |
| 31.43 | 2.84 | 3 |
| 32.40 | 2.76 | 22 |

Various modifications of the disclosure, in addition to those described herein, will be apparent to those skilled in the art from the foregoing description. Such modifications are also intended to fall within the scope of the appended claims. Each reference, including without limitation all patent, patent applications, and publications, cited in the present application is incorporated herein by reference in its entirety.

The invention claimed is:

1. A crystalline material having at least six XRD peaks selected from Table 1:

TABLE 1

| degree 2-theta (±0.20) | relative intensity [100 × I/(Io)] |
|---|---|
| 8.93 | 30-60 |
| 10.49 | 40-80 |
| 11.12 | 60-100 |
| 12.68 | 10-40 |
| 15.33 | 10-40 |
| 15.88 | 5-25 |
| 22.77 | 50-80 |
| 23.90 | 40-60 |
| 27.58 | 20-40 | wherein part or all of a structure directing agent has been removed from the crystalline material.

2. A crystalline material having a framework defined by the following connectivities in Table 2 for the tetrahedral (T) atoms in the unit cell, the tetrahedral (T) atoms being connected by bridging atoms:

TABLE 2

| T atom | Connected to: |
|---|---|
| T1 | T3, T5, T7, T9 |
| T2 | T5, T7, T8, T11 |
| T3 | T1, T4, T11, T12 |
| T4 | T3, T6, T9, T10 |
| T5 | T1, T2, T10, T13 |
| T6 | T4, T7, T12, T14 |
| T7 | T1, T2, T6, T13 |
| T8 | T2, T10, T12, T14 |
| T9 | T1, T4, T12, T14 |
| T10 | T4, T5, T8, T11 |
| T11 | T2, T3, T10, T13 |
| T12 | T3, T6, T8, T9 |
| T13 | T5, T7, T11, T14 |
| T14 | T6, T8, T9, T13 |

3. The material of claim 1 having a micropore volume of 0.10 to 0.28 cc/g.

4. The material of claim 1, wherein five of the six XRD peaks include the peaks in Table 1B:

TABLE 1B

| degree 2-theta (±0.20) | relative intensity [100 × I/(Io)] |
|---|---|
| 8.93 | 30-60 |
| 10.49 | 40-80 |

TABLE 1B-continued

| degree 2-theta (±0.20) | relative intensity [100 × I/(Io)] |
|---|---|
| 11.12 | 60-100 |
| 22.77 | 50-80 |
| 23.90 | 40-60 | and the crystalline material has a micropore volume of 0.10 to 0.28 cc/g.

5. The material of claim 1 having a composition including Formula I:

$$(m)X_2O_3{:}YO_2 \qquad \text{(Formula I)},$$

wherein $0.01 \leq m \leq 0.25$, X is a trivalent element, and Y is a tetravalent element.

6. The material of claim 5, wherein the ratio of Y to X is 5 to 25.

7. An as-made crystalline material having at least six XRD peak selected from Table 3:

TABLE 3

| degree 2-theta (±0.20) | relative intensity [100 × I/(Io)] |
|---|---|
| 8.73 | 20-40 |
| 10.37 | 20-60 |
| 11.04 | 60-100 |
| 12.56 | 20-40 |
| 17.52 | 30-70 |
| 19.45 | 30-70 |
| 20.47 | 30-70 |
| 22.40 | 50-80 |
| 23.83 | 20-60 |
| 27.18 | 30-70 |

8. The material of claim 7 having a triclinic unit cell a-parameter of 8.8±0.3 Å, b-parameter of 9.6±0.3 Å, c-parameter of 10.7±0.3 Å, α of 104±6°, β of 100±6°, and γ of 100±6°.

9. The material of claim 7 wherein the six XRD peaks include the peaks in Table 3B:

TABLE 3B

| degree 2-theta (±0.20) | relative intensity [100 × I/(Io)] |
|---|---|
| 8.73 | 20-40 |
| 10.37 | 20-60 |
| 11.04 | 60-100 |
| 17.52 | 30-70 |
| 19.45 | 30-70 |
| 22.40 | 50-80 | and the crystalline material has a triclinic unit cell a-parameter of 8.8±0.3 Å, b-parameter of 9.6±0.3 Å, c-parameter of 10.7±0.3 Å, α of 104±6°, β of 100±6°, and γ of 100±6°.

10. The material of claim 7 having a composition including Formula II:

$$(n)G{:}(v)X_2O_3{:}YO_2 \qquad \text{(Formula II)},$$

wherein $0.01 \leq v \leq 0.25$, $0.03 \leq n \leq 0.25$, G is an organic structure directing agent, X is a trivalent element, and Y is a tetravalent element.

11. The material of claim 10, wherein Y to X ratio is 5 to 25.

12. The material of claim 10, wherein the ratio of G to Y is 0.05 to 0.15.

13. A process of preparing the crystalline material of claim 7 comprising mixing a composition comprising a source of hydroxide ions, a source of an oxide of a tetravalent element Y, a source of a trivalent element X, and a structure directing agent (G) comprising a bispyrrolidinium dication.

14. The process of claim 13 further comprises removing part or all of the structure directing agent from the crystalline material.

\* \* \* \* \*